US012125562B2

(12) United States Patent
Chandak et al.

(10) Patent No.: US 12,125,562 B2
(45) Date of Patent: Oct. 22, 2024

(54) QUALITY VALUE COMPRESSION FRAMEWORK IN ALIGNED SEQUENCING DATA BASED ON NOVEL CONTEXTS

(71) Applicant: KONINKLIJKE PHILIPS N.V., Eindhoven (NL)

(72) Inventors: Shubham Chandak, Menlo Park, CA (US); Yee Him Cheung, Boston, MA (US)

(73) Assignee: Koninklijke Philips N.V., Eindhoven (NL)

( * ) Notice: Subject to any disclaimer, the term of this patent is extended or adjusted under 35 U.S.C. 154(b) by 0 days.

(21) Appl. No.: 17/797,146

(22) PCT Filed: Jan. 27, 2021

(86) PCT No.: PCT/EP2021/051782
§ 371 (c)(1),
(2) Date: Aug. 3, 2022

(87) PCT Pub. No.: WO2021/156110
PCT Pub. Date: Aug. 12, 2021

(65) Prior Publication Data
US 2023/0053844 A1   Feb. 23, 2023

Related U.S. Application Data (60) Provisional application No. 62/971,293, filed on Feb. 7, 2020.

(51) Int. Cl.
*G06F 16/00*   (2019.01)
*G06F 16/215*   (2019.01)
*G16B 30/10*   (2019.01)
*G16B 50/50*   (2019.01)

(52) U.S. Cl.
CPC ........... *G16B 50/50* (2019.02); *G06F 16/215* (2019.01); *G16B 30/10* (2019.02)

(58) Field of Classification Search
CPC ........ G06F 16/215; G16B 50/50; G16B 30/10
USPC ......................................................... 707/693
See application file for complete search history.

(56) References Cited

U.S. PATENT DOCUMENTS

2013/0204851 A1 * 8/2013 Bhola .................... G16B 30/10
707/693

OTHER PUBLICATIONS

Reggy Long et al., GeneComp, a new reference-based compressor for SAM files, 2017 Data Compression Conference, pp. 330-339. (Year: 2017).*
International Search Report and Written Opinion from PCT/EP2021/051782 mailed Apr. 28, 2021.
Reggy Long et al "CeneComp, a New Reference Based Compressor for SAM Files" 2017 Data Compression Conf. Apr. 4, 2017 p. 330-339.

(Continued)

*Primary Examiner* — Alexandria Y Bromell (57) ABSTRACT

A method for compressing information includes accessing a read of genomic sequencing data, aligning the read to a reference, generating alignment data based on alignment of the read, obtaining a set of contexts based on the alignment data, and compressing quality values corresponding to the alignment data based on the set of contexts. The alignment data may provide an indication of errors in the genomic sequencing data, and each of the quality values may provide an indication of a probability of error at one or more bases in the genomic sequencing data.

20 Claims, 7 Drawing Sheets

```
@SQ        SN:phix LN:5386
@PG        ID:minimap2    PN:minimap2    VN:2.17-r941    CL:minimap2 -ax sr -t 20 /raid/subham/private/philips/data/phi
x_hiseq2000/genome.fa /raid/shubham/private/philips/data/phix_hiseq2000/SRR1390645_1.fastq /raid/shubman/private/philip
s/data/phix_hiseq2000/SRR1390645_2.fastq
SRR1390645.1 99    phix    1    60    19SB2M    =    1    99    TTGGCGTATCCAACCTGCAGAGTTTTATCGCTTCCATGA
CGCAGAAGTTAACACTTTCGGATATTTCTGATGAGTCGAAAAATTATCTTGATAAAGCAGGA
FF>FFFCFFFGEGGGEDFGGGGFGGGGGGGGBGGGGFEGF?GFGECGF?GFGEG
GCCCFGF@EFEGGFE?EEA=7<<?@@GGECF@9@EEFFBFD,@@:F    NM:i:0    ms:i:164    AS:i:164    nn:i:0    tp:A:P    cm:i:10    s1:i:
89 s2:i:0    de:f:0    rl:i:0
SRR1390645.1 147    phix    1    58    2S99M    =    1    -99    CAGAGTTTTATCGCTTCCATGACGCAGAAGTTAACACTT
TCGGATATTTCTGATGAGTCGAAAAATTATCTTGATAAAGCAGGAATTACTACTGCTTGTTT
E9=5><<C<BCB>C>?=A8@DC@FFFE?EBDEEEEC;@=GBHEHHHIGGGGEAD
FBDECFFCF?FBGDFGFEHDFDHHHHHFHHHHHEHHCHHHEHFHHHH    NM:i:0    ms:i:198    AS:i:198    nn:i:0    tp:A:P    cm:i:4    s1:i:
89 s2:i:0    de:f:0    rl:i:0
SRR1390645.2 83    phix    1    60    2S99M    =    1    -99    CAGAGTTGTATCGCTTCCATGACGCAGAAGTTAACACTT
TCGGATATTTCTGATGAGTCGAAAAATTATCTTGATAAAGCAGGAATTACTACTGCTTGTTT
4?B>>?>(CCCDDD?@EBGGCEEEEBD@ED@CA?D=ECECGDEBGEDDEBBGDB
BGFFGAFFHHGHHHFHDHHHHGHHEHHHHHHFHHHHHHHHHHHHHHH    NM:i:1    ms:i:188    AS:i:188    nn:i:0    tp:A:P    cm:i:9    s1:i:
89    s2:i:0    de:f:0.0101    rl:i:0
```

(56) References Cited

OTHER PUBLICATIONS

Wenxian Yang et al "Improving Coding Efficiency of MPEG-G Standard Using Context Based Arithmetic Coding" 2018 EEE Int. Conf. on Bioinformatics and Biomedicine Dec. 3, 2018 p. 1177-1183.
Jan Voges, Jörn Ostermann, Mikel Hernaez, CALQ: compression of quality values of aligned sequencing data, Bioinformatics, vol. 34, Issue 10, May 15, 2018, pp. 1650-1658, https://doi.org/10.1093/bioinformatics/btx737.
Greg Malysa, Mikel Hernaez, Idoia Ochoa, Milind Rao, Karthik Ganesan, Tsachy Weissman, QVZ: lossy compression of quality values, Bioinformatics, vol. 31, Issue 19, Oct. 1, 2015, pp. 3122-3129, https://doi.org/10.1093/bioinformatics/btv330.
Bonfield, James K., and Matthew V. Mahoney. "Compression of FASTQ and SAM format sequencing data." PloS one 8.3 (2013): e59190.
Rissanen, Jorma, and Glen G. Langdon. "Arithmetic coding." IBM Journal of research and development 23.2 (1979): 149-162.
Guillermo Dufort, et al. "Compression of Nanopore FASTQ Files." International Work-Conference on Bioinformatics and Biomedical Engineering. Springer, Cham, 2019.
Goyal, Mohit, et al. "DeepZip: Lossless Data Compression using Recurrent Neural Networks." arXiv preprint arXiv:1811.08162 (2018).
Liu, Qian, Yiling Xu, and Zhu Li. "DecMac: A Deep Context Model for High Efficiency Arithmetic Coding." 2019 International Conference on Artificial Intelligence in Information and Communication (ICAIIC). IEEE, 2019.
Thorvaldsdottir, Helga, James T. Robinson, and Jill P. Mesirov. "Integrative Genomics Viewer (IGV): high-performance genomics data visualization and exploration." Briefings in bioinformatics 14.2 (2013): 178-192.
Li, Jundong, et al. "Feature selection: A data perspective." ACM Computing Surveys (CSUR) 50.6 (2018): 1994.
CRAM format specification (version 3.0), https://samtools.github.io/hts-specs/CRAMv3.pdf, accessed Aug. 8, 2019.
Alberti, Claudio, et al. "An introduction to MPEG-G, the new ISO standard for genomic information representation." bioRxiv (2018): 426353 Sep. 27, 2018.
Paridaens, T. et al., "AQUa: an adaptive framework for compression of sequencing quality scores with random access functionality", Bioinformatics, vol. 34, No. 3, (Sep. 25, 2017), pp. 425-433.

\* cited by examiner

```
@SQ     SN:phix LN:5386
@PG     ID:minimap2     PN:minimap2     VN:2.17-r941    CL:minimap2 -ax sr -t 20 /raid/subham/private/philips/data/phi
x_hiseq2000/genome.fa /raid/shubham/private/philips/data/phix_hiseq2000/SRR1390645_1.fastq /raid/shubman/private/philip
s/data/phix_hiseq2000/SRR1390645_2.fastq
SRR1390645.1  99   phix   1   60   19SB2M   =   1   99   TTGGGCGTATCCAACCTGCAGAGTTTATCGCTTCCATGA
CGCAGAAGTTAACACTTCTGGATATTTCTGATGAGTCGAAAAATTATCTTGATAAAGCAGGA
FF>FFFCFFFGEGGGEDFGGGGFGGGGGGGBGGGGGFEGF?GFECGF?GFGEG
GCCCFGF@EFEGGFE?EEA=7<<?@@GGECF@9@EEFFBFD,@@:F  NM:i:0  ms:i:164  AS:i:164  nn:i:0  tp:A:P  cm:i:10  s1:i:
89  s2:i:0  de:f:0  rl:i:0
SRR1390645.1  147  phix   1   58   2S99M   =   1   -99  CAGAGTTTATCGCTTCCATGACGCAGAAGTTAACACTT
TCGGATATTTCTGATGAGTCGAAAAATTATCTTGATAAAGCAGGAATTACTACTGCTTGTTT
E9=5><<<C<BCB>C>?=A8@DC@FFFE?EBDEEEEC;@=GBHEHHHIGGGGEAD
FBDECFFCF?FBGDFGFEHDFDHHHHFHHHHCHHHEHFHHHH  NM:i:0  ms:i:198  AS:i:198  nn:i:0  tp:A:P  cm:i:4  s1:i:
89  s2:i:0  de:f:0  rl:i:0
SRR1390645.2  83   phix   1   60   2S99M   =   1   -99  CAGAGTTGTATCGCTTCCATGACGCAGAAGTTAACACTT
TCGGATATTTCTGATGAGTCGAAAAATATCTTGATAAAGCAGGAATTACTACTGCTTGTTT
4?B>>?>(CCCDDD?@EBGGCEEEEBD@ED@CA?D=ECECGDEBGEDDEBBGDB
BGFFGAFFHHGHHHFHDHHHGHHEHHHHFHHHHHHHHHHHHH  NM:i:1  ms:i:188  AS:i:188  nn:i:0  tp:A:P  cm:i:9  s1:i:
89  s2:i:0  de:f:0.0101  rl:i:0
```

QUALITY VALUE COMPRESSION FRAMEWORK IN ALIGNED SEQUENCING DATA BASED ON NOVEL CONTEXTS

CROSS REFERENCE TO RELATED APPLICATIONS

This application is a U.S. national phase application of International Application No. PCT/EP2021/051782 filed on Jan. 27, 2021, which claims the benefit of U.S. Provisional Application No. 62/971,293 filed Feb. 7, 2020 and are incorporated herein by reference.

TECHNICAL FIELD

This disclosure relates generally to processing information, and more specifically, but not exclusively, to processing genome-related information.

BACKGROUND

Genomic sequencing typically produces large amounts of data in the form of reads (e.g., noisy substrings of a genome and corresponding quality values that provide an indication of the reliability, or confidence, in the read sequences. However, existing methods for compressing quality values of genomic sequencing data have drawbacks.

SUMMARY

A brief summary of various example embodiments is presented below. Some simplifications and omissions may be made in the following summary, which is intended to highlight and introduce some aspects of the various example embodiments, but not to limit the scope of the invention. Detailed descriptions of example embodiments adequate to allow those of ordinary skill in the art to make and use the inventive concepts will follow in later sections.

In accordance with one or more embodiments, a method for compressing information comprising (a) accessing a read of genomic sequencing data; (b) aligning the read to a reference; (c) generating alignment data based on alignment of the read; (d) obtaining a set of contexts based on the alignment data; (e) compressing quality values corresponding to the alignment data based on the set of contexts, wherein the alignment data provides an indication of errors in the genomic sequencing data and wherein each of the quality values provides an indication of a probability of error at one or more bases in the genomic sequencing data. The set of contexts may include at least one context.

The aligned genomic sequencing data may be compressed in (e) based on count-based adaptive arithmetic coding. The aligned genomic sequencing data may be compressed in (e) based on neural-network prediction-based arithmetic coding. The set of contexts may include a match between the read and a reference base. The set of contexts may include at least one of existence of a mismatch and type of mismatch. The set of contexts may include a number of bases in a reference sequence surrounding one or more of the quality values. The set of contexts may include mean quality value across a plurality of bases at one or more genomic coordinates. The set of contexts may include errors at current and nearby bases measured using a pileup of reads mapping to a same genomic coordinate. The operation (d) may include selecting the set of contexts based on one or more criteria, wherein the one or more criteria include dataset type, dataset size, context size, predictive power of context, or amount of data to be compressed.

In accordance with one or more embodiments, a system for compressing information comprising a memory configured to store instructions and a processor configured to execute the instructions to (a) access a read of genomic sequencing data; (b) align the read to a reference; (c) generate alignment data based on alignment of the read; (d) obtain a set of contexts based on the alignment data; (e) compress quality values corresponding to the alignment data based on the set of contexts, wherein the alignment data provides an indication of errors in the genomic sequencing data and wherein each of the quality values provides an indication of a probability of error at one or more bases in the genomic sequencing data. The set of contexts may include at least one context.

The processor may compress the aligned genomic sequencing data based on count-based adaptive arithmetic coding. The processor may compress the aligned genomic sequencing data in (e) based on neural-network, prediction-based arithmetic coding. The set of contexts may include a match between the read and a reference base. The set of contexts may include at least one of existence of a mismatch and type of mismatch. The set of contexts may include a number of bases in a reference sequence surrounding one or more of the quality values. The set of contexts may include mean quality value across a plurality of bases at one or more genomic coordinates. The set of contexts may include errors at current and nearby bases measured using a pileup of reads mapping to a same genomic coordinate. The operation (d) may include selecting the set of contexts based on one or more criteria, wherein the one or more criteria include dataset type, dataset size, context size, predictive power of context, or amount of data to be compressed.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to illustrate example embodiments of concepts found in the claims and explain various principles and advantages of those embodiments.

These and other more detailed and specific features are more fully disclosed in the following specification, reference being had to the accompanying drawings, in which.

DETAILED DESCRIPTION

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various example embodiments described herein are not necessarily mutually exclusive, as some example embodiments can be combined with one or more other example embodiments to form new example embodiments. Descriptors such as "first," "second," "third," etc., are not meant to limit the order of elements discussed, are used to distinguish one element from the next, and are generally interchangeable. Values such as maximum or minimum may be predetermined and set to different values based on the application.

Two platforms for sequencing genome data are (i) Illumina sequencing and (ii) Oxford nanopore (ONT) sequencing. Illumina sequencing offers high throughput, fixed length, and short read sequencing with very low error rates (<1%—mostly substitutions). ONT sequencing offers real-time, variable length, and long read sequencing with high error rates (10-15%—insertions, deletions and substitutions).

Raw sequencing data obtained from a sequencer implementing one or both of the aforementioned platforms may be aligned to a reference genome for further analysis, such as variant calling. The alignment is performed using standard tools that attempt to find the most similar section of the genome to each sequenced read in terms of a similarity metric such as Hamming distance or edit distance. Typical alignment tools include bwa for short read Illumina sequencing data and minimap2 for nanopore sequencing data. Both of these aligners use an indexing strategy to enable quick search of matches to the sequenced read in the genome.

Figure 1:
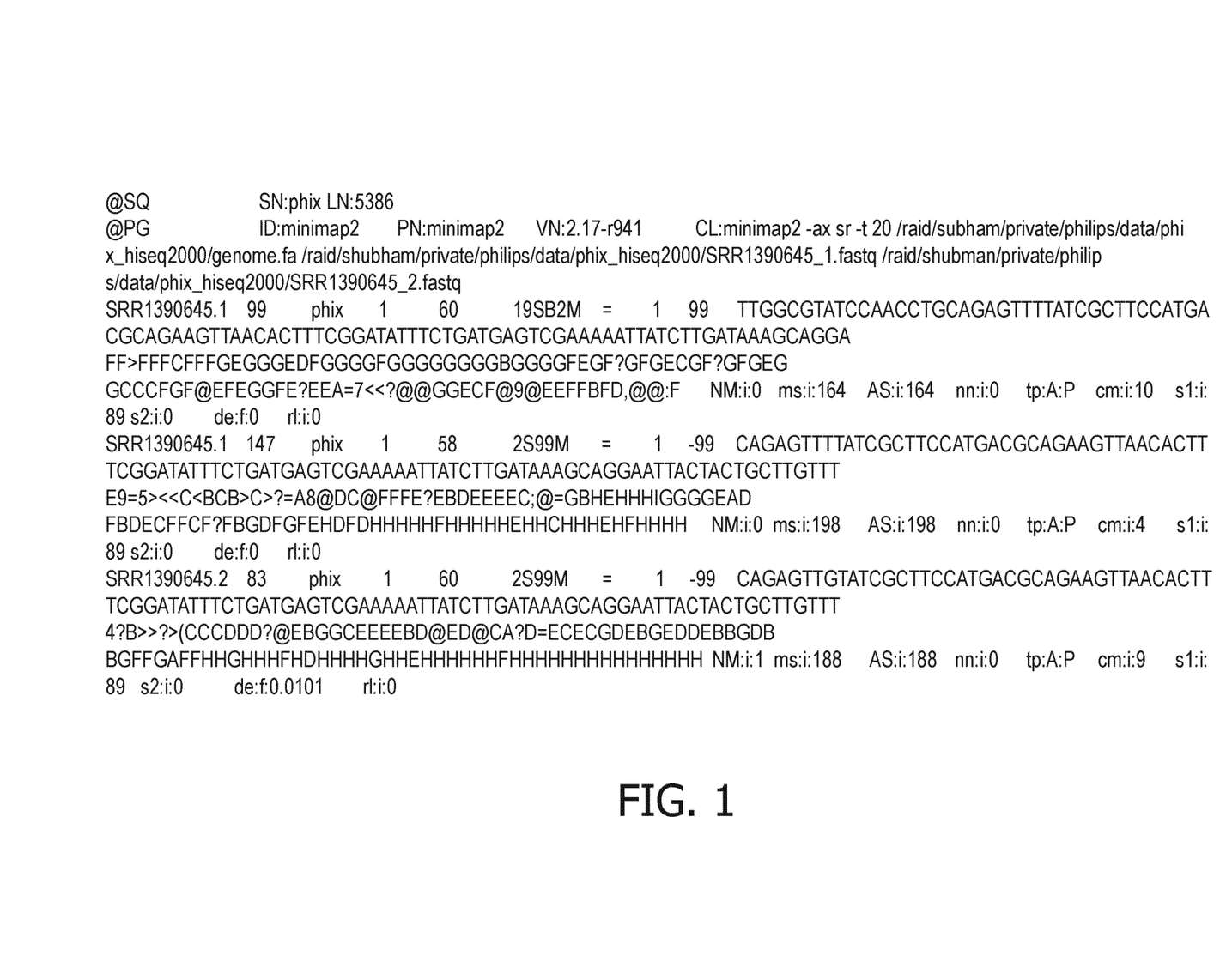
FIG. 1 illustrates an example of a sequence alignment map file.

The aligned genomic data may be represented using a file in sequence alignment map (SAM) format (or its compressed representations). An example of a SAM file is illustrated in FIG. 1. The file includes information about the sequence of nucleobases (A/C/G/T) in the read, the position of alignment, substitutions/insertions/deletions during alignment and associated quality values. The quality values may be represented, for example, as ASCII characters, but may be equivalently thought of as integer values (e.g., ranging from 0 to 40) representing the probability of error in a log scale.

Figure 2:
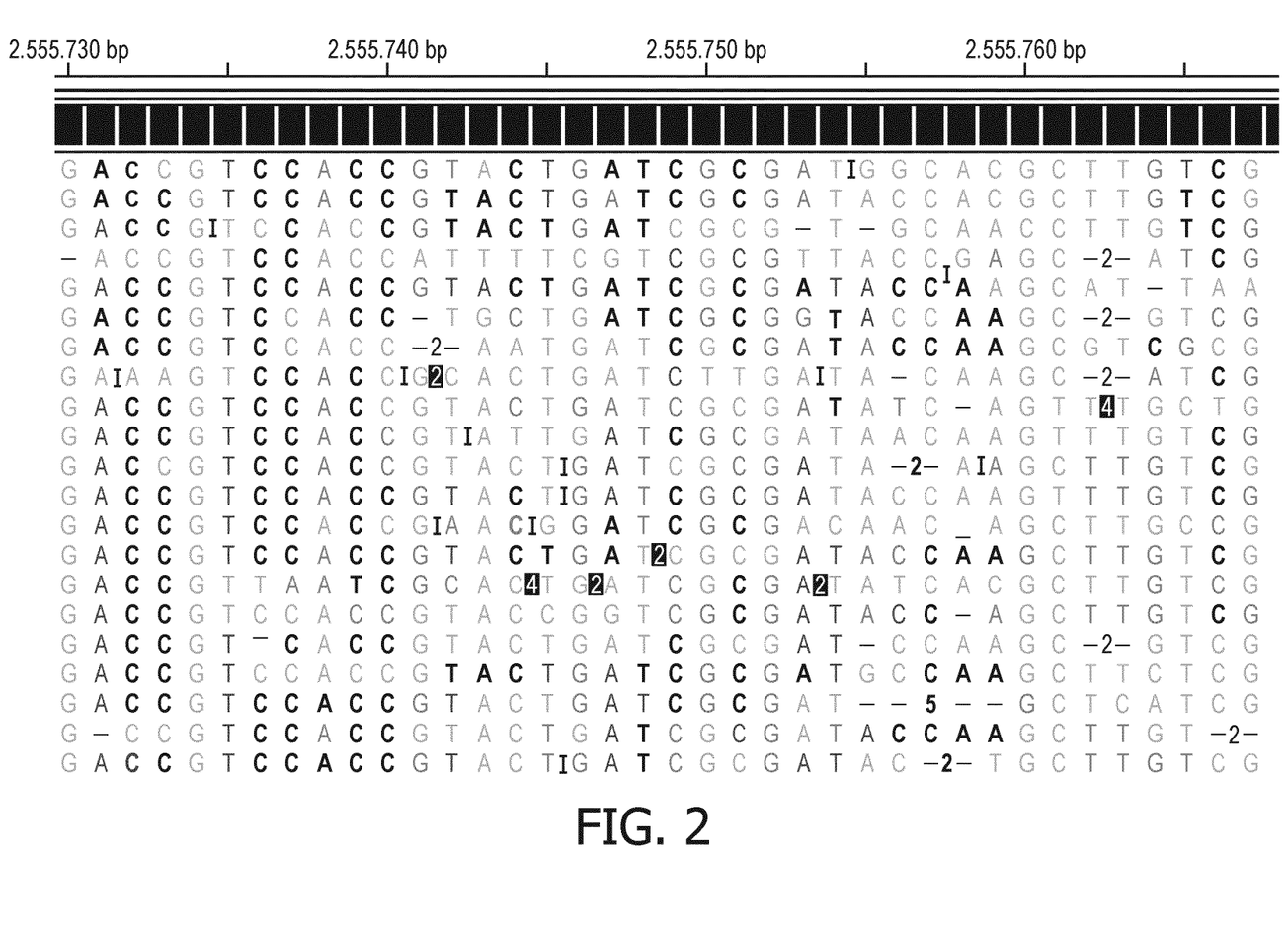
FIG. 2 illustrates an example of aligned genomic data with corresponding quality values.

FIG. 2 illustrates an example of genomic data with corresponding quality values. In this example, the quality values exhibit a dependence on genomic coordinates for a *K. pneumoniae* nanopore dataset. In FIG. 2, rows represent reads and columns represent genomic position. The shading of the symbols representing the nucleobases (C, T, A, G) represent quality values at corresponding genome positions, with brighter shading representing higher qualities. The quality values are produced by the base-calling process that converts the raw analog data from the sequencing technology to a sequence of most likely bases and the associated confidence in the prediction (quality values).

Figure 3:
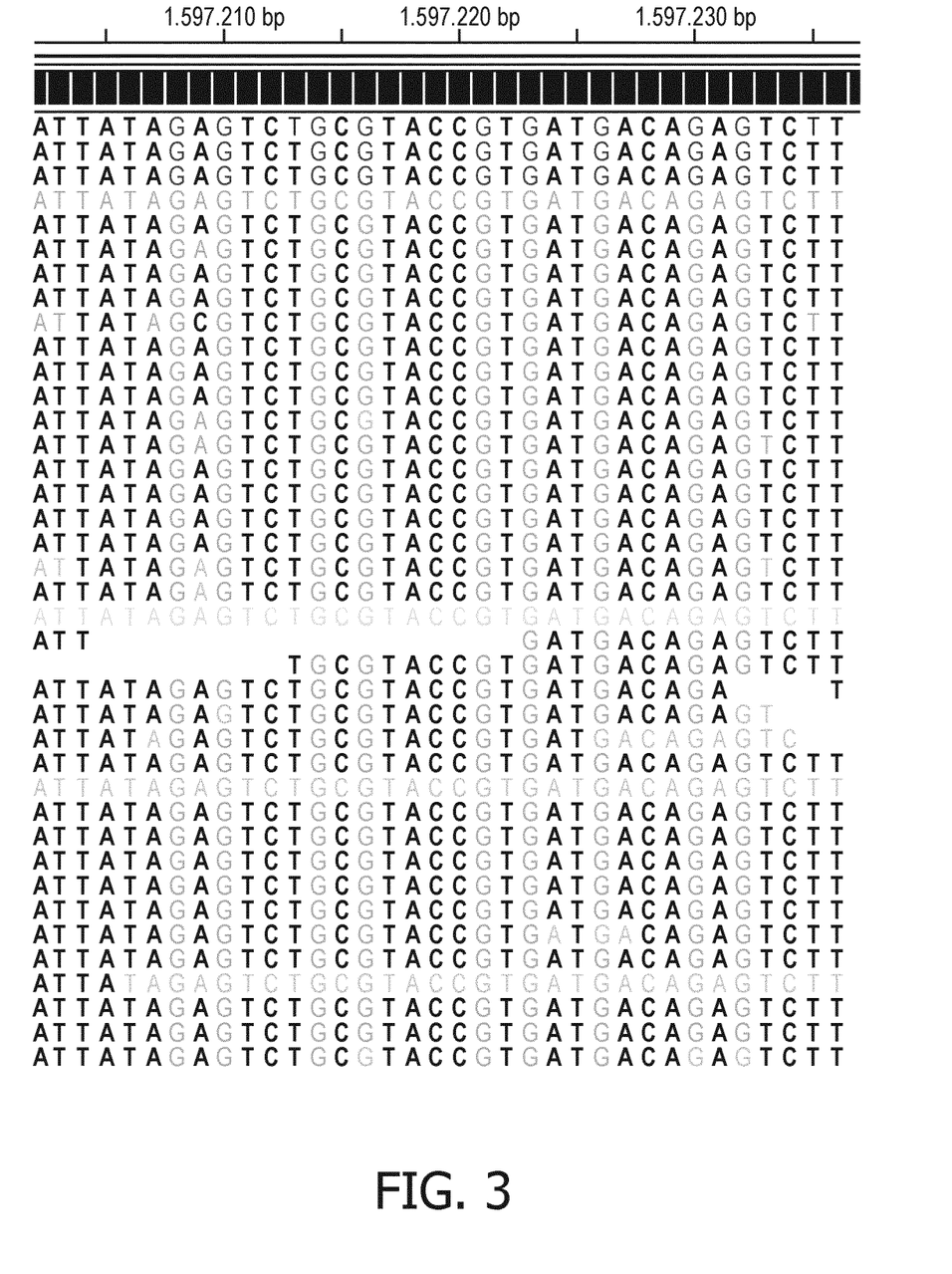
FIG. 3 illustrates an example of aligned genomic data with corresponding quality values.

FIG. 3 illustrates an example of the alignment of an Illumina MiSeq *E. coli* dataset, with rows representing reads and columns representing genome position. The shading of the symbols representing the nucleobases denotes the varying quality values at corresponding genome positions. In this example, there is little correlation between genomic coordinate and quality value. Instead, the correlation is mostly horizontal, e.g., qualities within a read. Due to their unpredictable nature and large alphabet size, quality values may be difficult to compress and may account for up to 80% of the size of compressed files after alignment.

Techniques for compressing quality values include lossy techniques and lossless techniques. Some types of lossy compression use alignment information to discard quality values when all reads agree at a genome position. In the case of Illumina sequencing, error rates may be relatively low and hence quality values may have less impact on analysis. In the case of Oxford nanopore sequencing, error rates may be relatively high and hence faithful preservation of quality values is more important for downstream applications. Note that nanopore sequencing provides several advantages over Illumina sequencing due to the long read lengths that enable structural variation analysis in the genome.

Lossless compression of quality values may involve, for example, arithmetic coding techniques or may be implemented using general-purpose universal compressors, like gzip or bzip2. Arithmetic coding may perform compression based on a (possibly adaptive) probabilistic model for the data. The better the model predicts the data, the better the compression. The model might incorporate various contexts that have statistical correlation with the data to be compressed. For arithmetic coding, a context of previous quality values may be used (e.g., order=number of previous quality values used as context). The probability model for each context may be updated based on the data already seen with that context. The size of the contexts may be chosen according to the size of the data. Otherwise, there may be insufficient data per context, which, in turn, may lead to poor probability model and compression. In one or more implementations, an order of 1 or 2 may suffice for Illumina sequencing datasets. In addition to previous quality values, compressors may also use position in read as a context in order to exploit the fact that quality values for Illumina sequencing become worse towards the end of the read, which is an effect that may not apply to nanopore sequencing.

Considering the increasing magnitude of genomic sequencing data and the contribution of quality values to overall size, one or more embodiments described herein provide improvements in the compression of quality values of genomic sequencing data. These embodiments include a system and method for generating and/or selecting one or more novel contexts to compress quality values of genomic data subject to an alignment process. The compression may be performed, for example, using count-based adaptive arithmetic coding or neural-network prediction-based arithmetic coding.

Compressing quality values based on alignment information may provide improved or optimal results for a number of reasons. For example, alignment information may provide an indication of errors that exist in the sequencing process, which may directly correspond to quality values that measure probability of error at a given base. Thus, alignment may provide "side-information" for quality value compression, which may lead to improved compression.

For nanopore sequencing, a correlation may exist between genomic coordinates and the quality values. In accordance with one or more embodiments, this correlation may be used as a basis for improving lossless quality value compression based on alignment information. For example, alignment information may be used to formulate novel contexts for predicting quality values, which may lead to improved prediction and compression using arithmetic coding.

In accordance with these or other embodiments, a neural-network, prediction-based arithmetic coding mode may be provided which does not treat quality values as discrete symbols, but rather treats quality values as related integers. For example, in accordance with one embodiment, a neural network may be provided which performs compression based on similarities of quality values that are adjacent to or come within a predetermined range of one another. Additionally, or alternatively, compression may be performed based on a similarity between base sequences (e.g., the nucleobase sequence ACGAT should be closer to the nucleobase sequence AGGAT than to the sequence GCCGA, where C is cytosine, T is thymine, A is adenine, and G is guanine). As opposed to count-based adaptive arithmetic coding, which considers each context value as independent, by using the contexts in the correct way, neural-network prediction-based arithmetic coding may be performed more accurately based on a large number of contexts, each having a significantly smaller data compared to, for example, other types of context-adaptive arithmetic coding.

Figure 4:
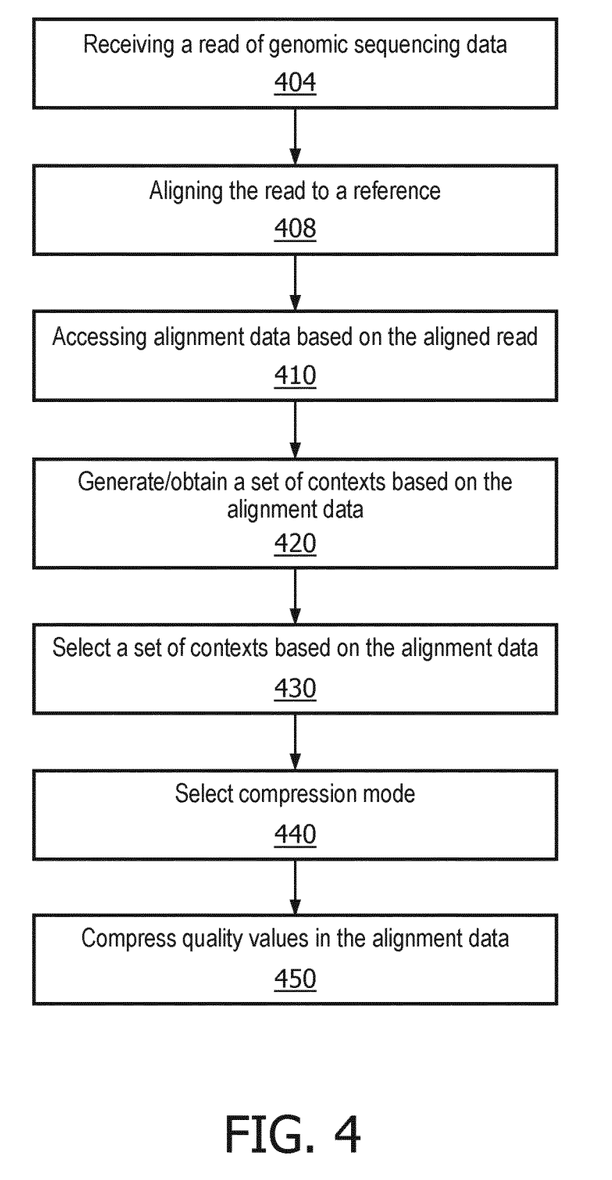
FIG. 4 illustrates an embodiment of a method for compressing genomic data.
Figure 5:
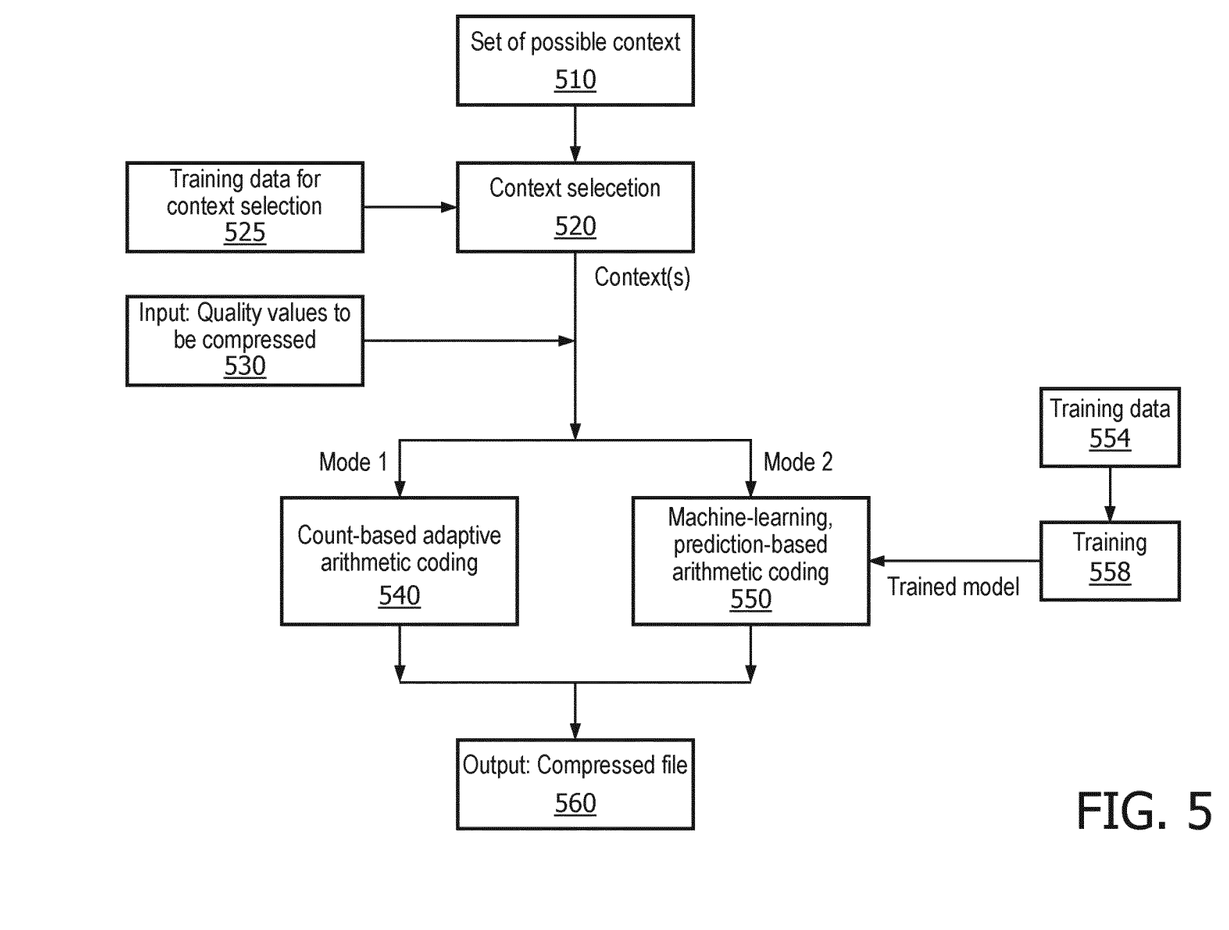
FIG. 5 illustrates an embodiment of a method for compressing genomic data.

FIG. 4 illustrates an embodiment of a method for compressing genomic data that includes quality values, and FIG. 5 provides a conceptual diagram of the compression method. Referring to FIGS. 4 and 5, the method includes, at 410, accessing information from a file containing genomic information. This operation may be preceded, for example, by an operation 404 which involves accessing a read of genomic sequencing data and an operation 408 which involves aligning the read to a reference. The file containing the genomic data may be, for example, a SAM file generated from the aligned read and may include a read identifier (id), alignment position of the read, a CIGAR string representing operations that transform the reference sequence into the read sequence, the read sequence, and quality values. The CIGAR string may indicate information relating to alignment. For example, when aligning a read sequence (e.g., sequence of nucleobases of C, T, A, and G) to a reference, there may be additional bases that are not in the reference and/or may be missing bases that are in the reference. A CIGAR string is a sequence of base lengths and associated operations, which may be used to indicate things like which bases align (match or mismatch) with the reference, are deleted from the reference, and/or insertions that are not in the reference. In another embodiment, the file may be different from a SAM file but may include the same or similar information.

At 420, a set of contexts 510 of the genomic sequencing data is obtained based on information (e.g., alignment data) in the file. In one embodiment, the contexts may be obtained from a set of possible contexts may already have been identified and stored in memory. In another embodiment, the set of contexts may be generated, for example, by a processor based on one or more criteria.

The set of contexts may include one or more contexts, which, for example, may refer to one or more conditions for correlating, organizing, collecting, or otherwise comparing the aligned genomic sensing data. These conditions may be used as a basis to model quality values, that predict the probability of the next quality value symbol, for example, used in arithmetic coding. In obtaining the set of contexts, it is noted that the file data may include aligned sequencing data with corresponding quality values. Therefore, access to the genomic coordinate where each base is aligned may be determined. The file data may also include information about reads mapping to genomic coordinate(s) and the presence and types of errors in the reads at the current and nearby genomic coordinates.

The set of contexts obtained in operation 420 are novel contexts, in the sense that they have not been previously used for processing genomic data (and especially with respect to the quality values of genomic data), nor have quality values of such data been compressed based on any of the types of contexts in the set. The set of contexts may be obtained in various ways. For example, in the case of a SAM file, the file may be parsed line-by-line, and for each quality value symbol one or more contexts may be generated based on fields in the SAM file and the reference genome sequence. For each context, the number of possible values (denoted as N) may be determined, which may prove relevant at least for count-based adaptive arithmetic coding.

In accordance with one or more embodiments, the set of novel contexts may include one or more of the following. The first context may be whether the read base matches the reference base. Whether or not this condition is satisfied may be indicated by a binary value (N=2), with the binary value set to 1 if the read base perfectly matches the reference base (as shown by the CIGAR string) and 0 if there is no match.

The second context may correspond to whether there is a mismatch, and if so what type of mismatch. The types of mismatch may include one or more of an insertion, deletion, or substitution. This information is typically contained in the CIGAR string in SAM file format and has N=4.

The third context may be k bases in a reference sequence surrounding a quality value. This may be obtained based on alignment position and the reference sequence, $N=4^k$.

The fourth context may be mean quality value across a plurality of bases at current and nearby genomic coordinates. The plurality of bases may be all or fewer than all bases at current and nearby coordinates. The mean quality value may be obtained by collecting all reads with an alignment that overlap with a specific base and then computing the mean value from the respective quality values as the specific base and nearby bases. In this case, N=(range of quality values). The mean quality value may be stored separately since this context may not be computed directly without the quality values themselves in certain circumstances. For example, the mean quality values at each genomic coordinate may be stored separately after compressing them with a compressor, e.g., a 7-zip. This may be performed so that the context may be computed at the decompressor, which may not have access to the next quality values in some cases.

The fifth context corresponds to errors at current and nearby bases measured using a pileup of reads mapping to the same genomic coordinate. In order to obtain this context, all reads having an alignment that overlaps with a specific base may be collected. Their pileup information, which represents the counts of bases aligning at the given positions, may then be taken which may be used as a basis for determining whether there is an error in the current read at a specific position or whether there is a difference between the sequenced data and the reference genome used for alignment. This context may be similar to the first context, except for the additional consideration that mismatch in the read relative to the reference might also be due to mutations, rather sequencing errors. There may be sixth and subsequent contexts as well, for example, any field in the aligned data may be used as a context for quality value compression.

In one embodiment, when using a set of contexts say $c\_1, c\_2, \ldots, c\_m$ from the contexts listed above, the set may be considered to be a single context denoted as a tuple $c=(c\_1, c\_2, \ldots, cm)$. If the number of possible values for context $c\_i$ is $N\_i$, then the number of possible values for the context c is $N\_1 \times N\_2 \times \ldots \times N\_m$. This context c may then be used as done in coding or for training of the neural network model.

In one embodiment, the context at step n may be computed without access to the qualities $q_n$ onwards, in order for decompression to be performed successfully. In one case, it may be assumed that the context takes value in a finite set, although that is not necessary for some forms of coding, e.g., machine-learning prediction-based arithmetic coding.

The context(s) obtained in operation 420 may also include other contexts which have been proposed previously. One context which has been proposed is Past k quality values for some k: $q_{n-1}, \ldots, q_{n-k}$. This context may be obtained directly from the quality value string in the SAM file. In this case, N=(range of quality values)$^k$, where the quality values may be in the range 40-80 (number of different quality values possible at each base). Another context which has been proposed is position in read. This may correspond to the position of the quality value symbol in the read of which it is a part, with N=maximum read length. Another context is k bases in a read surrounding the quality value. This may be obtained by selecting a k-length substring of the read sequence centered at a position in read, where $N=4^k$.

At 430, one or more contexts 520 in the set obtained in operation 420 are selected prior to compression (coding). Context selection may be performed in a variety of ways. For example, the context(s) may be selected based on one or more of the following criteria: type of dataset, size of dataset, size of the context, predictive power of the context, and amount of data to be compressed. In one embodiment, the context(s) to be selected may be determined based on the compression algorithm (e.g., coding mode) to be used. For some forms of coding (e.g., machine-learning), context selection may be performed based on a set of training data 525. The training data may indicate that a first set of contexts is to be selected for genomic data having a first set of characteristics or properties and that another set of contexts is to be selected for genomic data have a different, second set of characteristics or properties.

At 440, the coding mode is selected based on one or more predetermined criteria, including data size, prediction power, processing efficiency, availability of training data, compatibility with other systems or uses, and/or one or more other criteria or tradeoffs. In one embodiment, two possible entropy coding modes may be used: (1) Mode 1—count-based, adaptive arithmetic coding 540 and (2) Mode 2—machine-learning prediction-based arithmetic coding 550. Each type of coding has its own strengths and weaknesses. Once the mode is selected, a corresponding compression algorithm is applied to compress the quality values 530, which, for example, may be input from a SAM file.

Mode 1 may be implemented very efficiently relative to Mode 2, and may be beneficial for coding large amounts of genomic data. However, Mode 1 may have some limitations. For example, to achieve improved efficiency the amount of available data may have to be significantly larger than the set of all possible contexts. Insufficient data may lead to a counts array being sparsely filled and thus unable to provide a true probability distribution. These considerations may limit the number of contexts that can be used for prediction, for at least some applications. Also, the coding algorithm for Mode 1 may not always exploit similarities between context values (e.g., numerically similar quality values or similar sequences of bases). Since a counts array may separately count occurrences of each context value, more data may be needed in order to obtain a sufficient number of counts for each, even when there are similarities between them.

Mode 2 may solve these limitations by providing a much more powerful prediction framework which is able to exploit the contexts efficiently and ignore irrelevant contexts. The machine-learning, prediction-based arithmetic coding of Mode 2 may be performed based on a trained model 558 trained based on a set of training data 554. Mode 2 may provide improved results over Mode 1 in some circumstances. Nevertheless, Mode 1 may provide good, if not the best, results, for example, when large amounts of genomic sequencing data is available.

Figure 6:
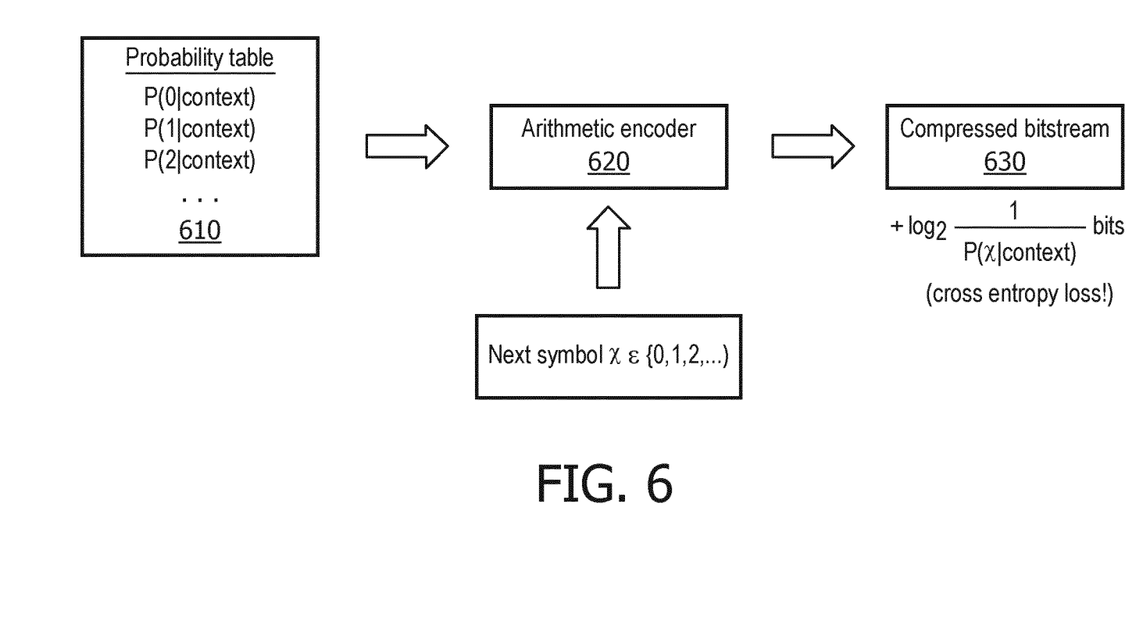
FIG. 6 illustrates an embodiment of an arithmetic coder for genomic data.

At 450, once the coding type has been selected, the quality values in the alignment data that are to be compressed are input into a compressor implementing the selected coding mode. An example of the inputs and outputs of the selected coder 620 is illustrated in FIG. 6. The inputs 610 may include predicted probabilities of the quality value symbols at each step (based on the context values), and the outputs 630 may include a compressed bitstream. In FIG. 6, $q_n$ denotes the $n^{th}$ quality value symbol. The overall context may be expressed as a tuple containing one or more of the possible contexts selected in a prior operation. Once compression is performed, the selected coder 620 may output a compressed file 560.

When Mode 1 is selected as the coding type to be implemented by the compressor, a count-based probability computation may be performed where the number of occurrences of each (context, quality) pair may be stored for use in computing the probability at each step. In one embodiment, the coding performed in Mode 1 may be performed as follows. First, initialize array counts [quality][context] to 1 for all (quality, context) pairs. Second, a size parameter is initialized to a zero value (in bits), representing the compressed size during the compression procedure. Then, for $q_n$ in the list of quality values, the context c is computed for $q_n$. The probability for the context is then computed according to: Prob (:|c)=counts[:][c]/sum(counts[:][c]). The value $q_n$ is then encoded with arithmetic encoding, using Prob(:|c) as the probability distribution. The size parameter is then adjusted, so that Size=Size+$\log_2$(1/Prob ($q_n$|c)). Finally, the count value is updated as counts[$q_n$][c]+=1.

When Mode 2 is selected as the coding type to be implemented by the compressor, a prediction model may be trained using the selected context(s) as input. During the training procedure, probabilities of each possible quality value may then be output, with a loss function being the categorical cross-entropy loss. Categorical cross-entropy loss is a standard loss function used in classification tasks which is relevant here since it also represents the compressed size on applying arithmetic coding with the predicted probabilities. The prediction model may be a machine-learning model, such as but not limited to a decision tree, neural network, one or more linear filters, or another type of model. For the model input, the quality values may be treated, for example, as numerical (instead of categorical) and the other contexts may be incorporated as categorical or numerical variables.

The compressor may perform the following operations in implementing Mode 2. First, the size parameter is initialized to zero (in bits), representing the compressed size during the compression procedure. Second, for $q_n$ in the list of quality values, compute context c for $q_n$. Then, the probability Prob (:|c) is generated by the prediction model by setting the input to c. The size is then adjusted as follows: Size=Size+$\log_2$ (1/Prob ($q_n$|c)). In an optional operation, adaptive training on the prediction model may be performed based on ($q_n$, c). This adaptive training operation may be used in both modes of a training procedure, discussed in greater detail below, to give a total of 4 possible modes of operation. In some cases, this operation may increase the computation time, but may improve compression when the training data is not available or when a mismatch exists between the training data and the data to be compressed.

The model used in Mode 2 coding may be trained in various ways. For example, training of the model may be performed on the data to be compressed. In this case the trained model parameters (e.g., after compression with a tool like 7-zip) may be included as part of the compressed file. This information may be included in the file so that the decompressor can perform the same operations as the compressor in order to decompress the compressed data. Another training technique may involve training the model on a dataset that is distinct from the data to be compressed. In this case, the model may be shared between the encoder and decoder. Here, there is no need to include the model parameters in the file if they are already known to the decoder. The first training procedure mentioned above may be useful, for example, when similar datasets for training are not available. The second training procedure may be more efficient in terms of compression time and compressed size in some cases.

Decompression may be performed in a manner symmetrical to the compression performed to compress the aligned data. For example, the arithmetic coder may be replaced with an arithmetic decoder that performs inverse operations of the Mode 1 or Mode 2 compression that was performed.

Figure 7:
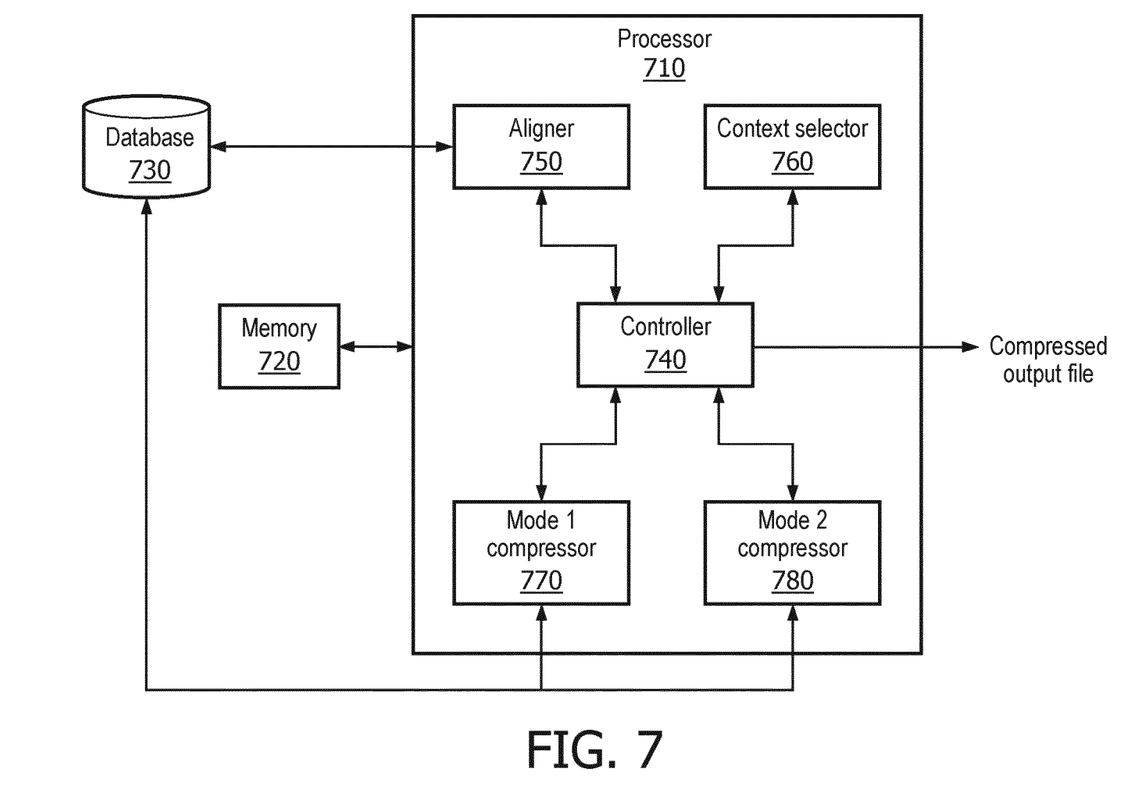
FIG. 7 illustrates an embodiment of a system for compressing genomic data.

FIG. 7 illustrates an embodiment of a system for compressing genomic sequencing data, which, for example, may perform the method embodiments described herein. The system includes a processor 710, a memory 720, and a database 730. The processor includes a controller 740, an aligner 750, a context selector 760, a Mode 1 compressor 770, and a Mode 2 compressor 780. The processor may perform or control the operations of the method embodiments, by executing instructions stored in the memory 720, which, for example, may be a non-transitory computer-readable medium. Examples of memory 720 include a read-only memory or a random-access memory, including various types of these memories.

The aligner 740 may align a read of genomic sequencing data stored in database 730 to a predetermined reference. The processor may generate alignment data based on alignment of the read. The alignment data may be stored in the database along with the genomic sequencing data. The context selector 750 may select a set of contexts based on the alignment data, and the controller may select one of the Mode 1 and Mode 2 compressors based on the criterial or other conditions discussed herein. The processor may then receive the results from the selected compressor and output a compressed file to a workstation or other terminal, for storage in database 730, or both. The compressors may be replaced by, or configured to operate as, corresponding decompressors in order to decompress the output file at a subsequent time.

EXAMPLE

During testing, the aforementioned embodiments were applied to compress one Illumina dataset and two nanopore datasets of genomic data. Table 1 shows the datasets used for evaluation. For simplicity, only aligned reads mapping to the forward strand were used in the experiments.

TABLE 1

| Organism | e. coli | lambda phage | k. pneumoniae |
|---|---|---|---|
| Genome length | 4641652 | 48502 | 5111537 |
| Sequencing technology | Illumina MiSeq | ONT | ONT |
| Number of reads | 458238 | 747 | 8143 |
| Coverage | 30 | 94 | 54 |
| Uncompressed quality size (B) | 137800413 | 4540484 | 278713931 |

For the Illumina dataset, the results show a very slight improvement (0.6%) by incorporating the additional context denoting the presence of mismatches, while other contexts are less effective. This is to be expected because the error rates in Illumina are very low, leading to most quality values being uninformative. Furthermore, there is little dependence between the read/reference sequence and the quality values for Illumina sequencing.

For the nanopore datasets, the results show a more significant improvement. For the smaller lambda phage dataset, using mismatch type and mean quality value at genomic coordinates as additional contexts (with 1 previous quality value) improved the compression by 2.4% in Mode 1. Due to the small dataset size, using more contexts in Mode 1 may make the results worse. On the other hand, compression in Mode 2 allows for use of a greater number of contexts and provided a further 4% improvement. The set of contexts used in this case was two previous quality values, mean quality value at genomic coordinates, five nearby bases in read, and the compression was performed by a neural network model using a 3-hidden layer fully connected network with a width of 20. The model was trained using the first training procedure as previously described (i.e., training performed on the data to be compressed) for 20 epochs (ReLU non-linearity, batch normalization, softmax activation used). Further improvements may be possible with more powerful models like RNNs and associated training procedures.

In Mode 1 compression experiments on the larger *K. pneumoniae* dataset, the results showed improvements close to 6% when using alignment information (with contexts of give nearby bases in reference and mismatch type) and previous qualities vs. using only previous qualities. Further improvements of Mode 1 were obtained using a context of nearby read bases and previous quality values, giving a further 2% improvement.

Additional experiments were performed on a subset of this dataset using Mode 2 compression using the context of the size of the dataset and with compression not optimized for speed. The results shows at least a 2% improvement over Mode 1 compression, even when using a small fully connected neural network.

Thus, using additional contexts derived from alignment may provide a boost of around 5% or more for the quality value compression. The choice of the set of contexts is significant for Mode 1 compression, but may be less significant for Mode 2 compression—where the results are even better but at the cost of increased computation time. Further optimization is possible for speed, for the choice of contexts, and for the neural network architecture and training procedure.

Another embodiment includes a computer-readable medium storing instructions for causing a processor to perform the operations of the embodiments described herein. Additional instructions may be stored in the computer-readable medium to perform other operations of the system and method embodiments.

The processors, controllers, compressors, decompressors, coders, decoders, selectors, aligners, and other information generating, processing, and calculating features of the embodiments disclosed herein may be implemented in logic which, for example, may include hardware, software, or both. When implemented at least partially in hardware, the processors, controllers, compressors, decompressors, coders, decoders, selectors, aligners, and other information generating, processing, and calculating features may be, for example, any one of a variety of integrated circuits including but not limited to an application-specific integrated circuit, a field-programmable gate array, a combination of logic gates, a system-on-chip, a microprocessor, or another type of processing or control circuit.

When implemented in at least partially in software, the processors, controllers, compressors, decompressors, coders, decoders, selectors, aligners, and other information generating, processing, and calculating features may include, for example, a memory or other storage device for storing code or instructions to be executed, for example, by a computer, processor, microprocessor, controller, or other signal processing device. Because the algorithms that form the basis of the methods (or operations of the computer, processor, microprocessor, controller, or other signal processing device) are described in detail, the code or instructions for implementing the operations of the method embodiments may transform the computer, processor, controller, or other signal processing device into a special-purpose processor for performing the methods herein.

Although the various exemplary embodiments have been described in detail with particular reference to certain exemplary aspects thereof, it should be understood that the invention is capable of other example embodiments and its details are capable of modifications in various obvious respects. As is readily apparent to those skilled in the art, variations and modifications can be affected while remaining within the spirit and scope of the invention. The embodiments may be combined to form additional embodiments. Accordingly, the foregoing disclosure, description, and figures are for illustrative purposes only and do not in any way limit the invention.

We claim:

1. A method for compressing genomic information, comprising:
   (a) accessing a read of genomic sequencing data;
   (b) aligning the read to a reference;
   (c) generating alignment data, which comprises an alignment position on the reference and a characterization of matches and mismatches of bases in the read compared to bases in the reference at alignment position, such as a CIGAR representation, after alignment of the read;
   (d) arithmetically compressing quality values of the read, wherein each of the quality values provides an indication of a probability of error of a base in the genomic sequencing data, wherein the compressing comprises:
   (e) selecting a set of one or more arithmetic compression contexts, characterized in that at least one of the arithmetic compression contexts is based on the alignment data, wherein at least one of the arithmetic compression contexts based on the alignment data is based on neural-network prediction-based arithmetic coding, and wherein the at least one of the arithmetic compression contexts based on the alignment data comprises selecting from:
   whether the base in the read at the position of the quality value matches the base in the reference;
   the type of mismatch at the position of the quality value, being an insertion, deletion, or substitution,
   the type of bases in the reference surrounding the position on the reference corresponding to the position of the quality value in the read, and
   a mean quality value of bases surrounding the position on the reference corresponding to the position of the quality value in the read.

2. The method of claim 1, wherein the aligned genomic sequencing data is compressed in (e) based on count-based adaptive arithmetic coding.

3. The method of claim 1, wherein the aligned genomic sequencing data is compressed in (e) based on arithmetic coding, with the arithmetic coding mode and training procedure chosen based on one or more criteria, wherein the one or more criteria include data size, prediction power, processing efficiency, availability of training data, or compatibility with other systems or uses.

4. The method of claim 1, wherein the set of contexts includes a match between the read and a reference base.

5. The method of claim 1, wherein the set of contexts includes at least one of existence of a mismatch or a type of mismatch.

6. The method of claim 1, wherein the set of contexts includes a number of bases in a reference sequence surrounding the position in the reference sequence corresponding to a quality value to be compressed.

7. The method of claim 1, wherein the set of contexts includes mean quality value across a plurality of bases at current or nearby genomic coordinates.

8. The method of claim 1, wherein the set of contexts includes errors at current and nearby bases measured using a pileup of reads mapping to the same genomic coordinate.

9. The method of claim 1, wherein step (e) includes:
   selecting the set of contexts based on one or more criteria, wherein the one or more criteria include dataset type, dataset size, context size, predictive power of context, or amount of data to be compressed.

10. A system for compressing information, comprising:
    a memory configured to store instructions; and
    a processor configured to execute the instructions to:
    (a) access a read of genomic sequencing data;
    (b) align the read to a reference;
    (c) generate alignment data based on alignment of the read, which comprises an alignment position on the reference and a characterization of matches and mismatches of bases in the read compared to bases in the reference at alignment position, such as a CIGAR representation;
    (d) obtain a sequence of quality values for the read, wherein each of the quality values provides an indication of a probability of error of a base in the genomic sequencing data,
    (e) select a set of one or more arithmetic encoding contexts, characterized in that these one or more arithmetic encoding contexts are based on the alignment data, wherein at least one of the arithmetic compression contexts based on the alignment data is based on neural-network prediction-based arithmetic coding, and wherein the at least one of the arithmetic compression contexts based on the alignment data comprises is selected from:

whether the base in the read at the position of the quality value matches the base in the reference;

the type of mismatch at the position of the quality value, being an insertion, deletion or substitution, the type of bases in the reference surrounding the position on the reference corresponding to the position of the quality value in the read, and a mean quality value of bases surrounding the position on the the reference corresponding to the position of the quality value in the read; and (f) arithmetically compress the quality values using the set of contexts.

11. The system of claim 10, wherein the processor is to compress the aligned genomic sequencing data based on count-based adaptive arithmetic coding.

12. The system of claim 10, wherein the processor is to compress the aligned genomic sequencing data based on arithmetic coding, with the arithmetic coding mode and training procedure chosen based on one or more criteria, wherein the one or more criteria include data size, prediction power, processing efficiency, availability of training data, or compatibility with other systems or uses.

13. The system of claim 10, wherein the set of contexts includes a match between the read and a reference base.

14. The system of claim 10, wherein the set of contexts includes at least one of existence of a mismatch or a type of mismatch.

15. The system of claim 10, wherein the set of contexts includes a number of bases in a reference sequence surrounding a position in the reference corresponding to a quality value to be compressed.

16. The system of claim 10, wherein the set of contexts includes mean quality value across a plurality of bases at current or nearby genomic coordinates.

17. The system of claim 10, wherein the set of contexts includes errors at current and nearby bases measured using a pileup of reads mapping to the same genomic coordinate.

18. The system of claim 10, wherein (e) includes:
selecting the set of contexts based on one or more criteria, wherein the one or more criteria include dataset type, dataset size, context size, predictive power of context, or amount of data to be compressed.

19. A method of decompressing genomic information which was compressed
according to the method of claim 1.

20. A system of decompressing genomic information which was compressed using a
system as claimed in claim 10.

* * * * *